United States Patent
Crane et al.

(10) Patent No.: US 7,140,126 B2
(45) Date of Patent: *Nov. 28, 2006

(54) GEL INSOLES WITH LOWER HEEL AND TOE RECESSES HAVING THIN SPRING WALLS

(75) Inventors: Laura J. Crane, Williston, TN (US); Richard Avent, Bartlett, TN (US); Donald Barry Thompson, Raleigh, NC (US)

(73) Assignee: Schering-Plough Healthcare Products, Inc., Kenilworth, NJ (US)

( * ) Notice: Subject to any disclaimer, the term of this patent is extended or adjusted under 35 U.S.C. 154(b) by 302 days.

This patent is subject to a terminal disclaimer.

(21) Appl. No.: 10/612,539

(22) Filed: Jul. 2, 2003

(65) Prior Publication Data

US 2004/0003513 A1    Jan. 8, 2004

Related U.S. Application Data

(63) Continuation of application No. 10/026,571, filed on Dec. 20, 2001, now Pat. No. 6,598,321, which is a continuation of application No. 09/803,706, filed on Mar. 9, 2001, now abandoned, which is a continuation of application No. 09/454,980, filed on Dec. 3, 1999, now abandoned.

(51) Int. Cl.
  *A43B 13/40* (2006.01)
  *A43B 13/18* (2006.01)
(52) U.S. Cl. .................................. 36/43; 36/27; 36/28

(58) Field of Classification Search .................... 36/43, 36/27, 28, 29, 141, 44
See application file for complete search history.

(56) References Cited

U.S. PATENT DOCUMENTS

| | | | |
|---|---|---|---|
| 4,486,964 A | | 12/1984 | Rudy |
| 4,557,060 A | | 12/1985 | Kawashima |
| 4,627,179 A | | 12/1986 | McElroy |
| 4,760,655 A | | 8/1988 | Mauch |
| 4,808,469 A | * | 2/1989 | Hiles ............................. 36/44 |
| 4,841,647 A | | 6/1989 | Turucz |
| 4,879,821 A | * | 11/1989 | Graham et al. ................ 36/44 |
| 4,977,691 A | * | 12/1990 | Orchard, 3rd .................. 36/44 |
| 5,469,639 A | * | 11/1995 | Sessa ............................ 36/28 |

(Continued)

*Primary Examiner*—Ted Kavanaugh
(74) *Attorney, Agent, or Firm*—Matthew J. Golden

(57) ABSTRACT

A removable insole for insertion into footwear, includes a lower layer made of a viscoelastic gel and including a lower surface, an upper surface, a toe portion, a heel portion and a medial arch portion interconnecting the toe portion and the heel portion, a first recess formed in the lower surface of the toe portion and a second recess formed in the lower surface of the heel portion, each recess having a peripheral side wall and a top wall, a plurality of thin, parallel, spaced apart sinusoidal wave shaped spring walls formed from the viscoelastic gel and connected to the top wall and the peripheral side wall in each recess, and the spring walls having lower edges generally coplanar with a lower surface of the toe portion and heel portion which is in surrounding relation to the respective recess; and a top cover secured to the upper surface of the lower layer.

16 Claims, 10 Drawing Sheets

U.S. PATENT DOCUMENTS

| | | |
|---|---|---|
| 5,488,786 A | 2/1996 | Ratay |
| 5,517,770 A * | 5/1996 | Martin et al. ............... 36/43 |
| 5,542,196 A | 8/1996 | Kantro |
| 5,551,173 A | 9/1996 | Chambers |
| 5,611,153 A * | 3/1997 | Fisher et al. ............... 36/43 |
| D389,296 S * | 1/1998 | Sessa ............... D2/961 |
| 5,766,704 A | 6/1998 | Allen et al. |
| 6,598,321 B1 | 7/2003 | Crane |

\* cited by examiner

GEL INSOLES WITH LOWER HEEL AND TOE RECESSES HAVING THIN SPRING WALLS

This application is a continuation of 10/026,571 filed on Dec. 20, 2001 now U.S. Pat. No. 6,598,321 which is a continuation of 09/803,706 filed on Mar. 9, 2001 now abandoned which is a continuation of 09/454,980 filed Dec. 3, 1999 now abandoned.

BACKGROUND OF THE INVENTION

The present invention relates generally to shoe insoles, and more particularly, to improved gel insoles for shoes that provide both cushioning and spring characteristics.

Insoles have generally been formed by a pad of cushioning material, such as foam or sponge rubber, that has a general shape conforming to the interior of a shoe. Wearers who desire additional shoe comfort or who suffer from foot trouble, for example, plantar heel pain and/or arch pain, insert the cushioned insole into the shoe to provide added cushioning and support.

It is also known to provide gel insoles for shoes. The gel insoles are provided as a movable fluid or as a viscoelastic gel. Because of the viscous nature of the gel, the gel insoles provide shock absorption and consequently protection to the foot. One reason that gel insoles are popular is that they can be made sufficiently thin to fit in shoes. In order to provide comfort, a soft, absorbent top cloth is adhered to the upper surface of the gel insoles.

However, the shock absorbing quality of the gel insoles has a deleterious effect. Specifically, because of the dampening affect of the gel, walking can require more energy, causing the muscles to get tired more easily.

U.S. Pat. No. 5,551,173 to Chambers discloses an insole having oblong protuberances on the upper surface and located in areas corresponding to the reflex zones of the feet, to provide a massaging action thereat. It is further disclosed in this patent that the insoles can be reversed so that the protuberances are on the lower surface of the insoles for the purpose of raising the insoles to provide air circulation. However, because of the composition of the insoles and the shapes of the protuberances, the protuberances do not substantially aid in reducing the energy during walking.

SUMMARY OF THE INVENTION

Accordingly, it is an object of the present invention to provide a gel insole that overcomes the problems with the aforementioned prior art.

It is another object of the present invention to provide a gel insole that provides the shock dampening affect of a gel material, while also providing a spring action push-off for walking.

It is still another object of the present invention to provide a gel insole that provides comfort to a person's feet, without causing the muscles to tire easily.

In accordance with an aspect of the present invention, a removable insole for insertion into footwear, includes a lower layer made of a viscoelastic gel and including a lower surface, an upper surface, and at least one of a toe portion and a heel portion formed from the viscoelastic gel. At least one recess is formed in the lower surface of the toe portion and/or heel portion, each recess having a peripheral side wall and a top wall. A plurality of spaced apart spring walls formed from the viscoelastic gel are provided in each recess, the spring walls being connected with the top wall of the respective recess, and the spring walls having lower edges generally coplanar with a lower surface of the toe portion and/or heel portion which is in surrounding relation to the respective recess. A top cover is secured to the upper surface of the lower layer.

Preferably, when a recess is formed in the heel portion, each of the spring walls has a height in a first direction which is greater than a width thereof in a direction transverse to the first direction.

In one embodiment, each of the spring walls is formed in a generally sinusoidal wave shape, with the plurality of spring walls being in substantially parallel, spaced apart relation. A spacing between adjacent ones of the spring walls is greater than the width of the spring walls. Further, the sinusoidal wave shaped spring walls are connected with the peripheral side wall and the top wall of the respective recess.

In another embodiment, the spring walls are formed as column members, in parallel, spaced apart relation. Each of the column members can have a cylindrical shape, a triangular cross-sectional shape, or any other suitable cross-section. When a recess is formed in the heel portion, each of the spring walls has a height in a first direction which is greater than a width thereof in a direction transverse to the first direction. Also, a spacing between adjacent ones of the spring walls is preferably greater than the width of the spring walls. The spring walls are connected with the top wall of the respective recess.

The insole also includes at least one pattern trim line at the toe portion for trimming the insole to fit into smaller size footwear.

Preferably, the lower layer includes the toe portion, the heel portion and a medial arch portion interconnecting the toe portion and the heel portion, with a first recess with the spring walls in the toe portion and a second recess with the spring walls in the heel portion. In such case, the heel portion has a greater thickness than the toe portion, and the spring walls in the second recess having a greater height than the spring walls in the first recess. Also, opposite sides of the medial arch portion and opposite sides and a rear end of the heel portion gently slope downwardly and inwardly toward the lower surface of the lower layer.

The above and other features of the invention will become readily apparent from the following detailed description thereof which is to be read in connection with the accompanying drawings.

DETAILED DESCRIPTION

Figure 1:
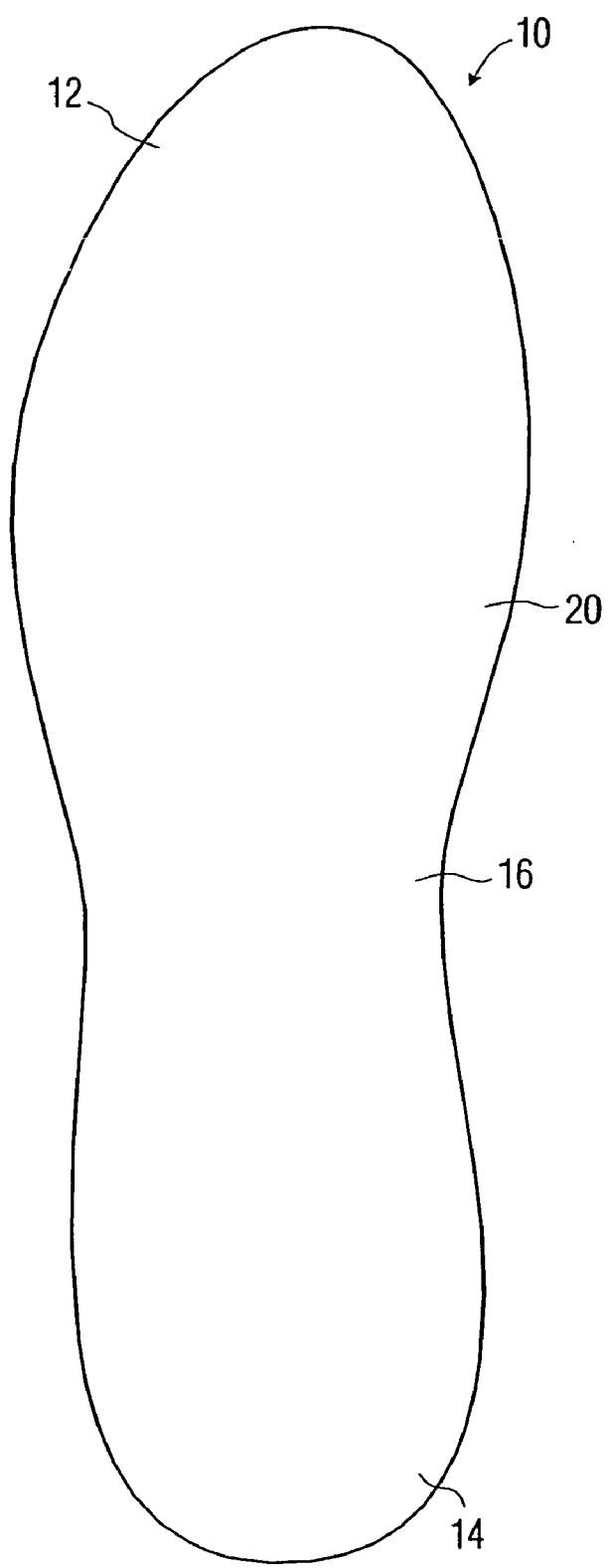
FIG. 1 is a top plan view of a gel insole according to one embodiment of the present invention.

Referring to the drawings in detail, and initially to FIGS. 1–7 thereof, an insole 10 according to a first embodiment of the present invention is adapted to be placed in an article of footwear, as is well known. Accordingly, insole 10 has the shape of a human left foot and has a companion (not shown) for the right foot which is formed in a mirror image.

Insole 10 therefore includes a curved toe portion 12, a heel portion 14, and a medial arch portion 16 which connects toe portion 12 and heel portion 14 together. Heel portion 14 has a greater thickness than toe portion 12 since the greater impact during walking and running occurs at the heel. For example, in the embodiment of FIGS. 1–7, heel portion 14 can have a thickness of approximately 7–8 mm and toe portion 12 can have a thickness of approximately 2–3 mm. In addition, opposite sides of medial arch portion 16, and opposite sides and the rear end of heel portion 14, gently slope downwardly and inwardly toward the lower surface of insole 10.

Insole 10 is formed of a lower gel layer 18 and a top cover 20 secured to the upper surface of lower gel layer 18 by any suitable means, such as adhesive, RF welding, etc. Both layers 18 and 20 are preferably formed of a fluid impermeable material.

Lower gel layer 18 is made from a non-foam elastomer such as the class of materials known as viscoelastic polymers or silicone gels, which show high levels of damping when tested by dynamic mechanical analysis performed in the range of –50° degrees C. to 100° degrees C. Because the mechanical properties of the gel are more viscous than elastic, the gel provides a high energy absorption. Gels that can be used according to the present invention are thermoplastic elastomers (elastomeric materials), such as materials made from many polymeric families, including but not limited to the Kraton family of styrene-olefin-rubber block copolymers, thermoplastic polyurethanes, thermoplastic poly olefins, polyamides, polyureas, polyesters and other polymer materials that reversibly soften as a function of temperature. The preferred elastomer is a Kraton block copolymer of styrene/ethylene-co-butylene/styrene or styrene/butadiene/styrene with mineral oil incorporated into the matrix as a plasticizer.

However, as discussed above, because of the dampening affect of the gel, walking can require more energy, causing the muscles to get tired more easily.

In this regard, in accordance with an important aspect of the present invention, thin and spaced apart elastic and resilient spring walls 22 are formed in a repeating order within a recess 24 formed in toe portion 12. Recess 24 occupies a substantial central area of toe portion 12, with thin spring walls 22 extending substantially transversely from one side to the other side of recess 24 and integrally formed as a unitary, one-piece structure with the peripheral side wall 28 and top wall 34 of recess 24. The height of spring walls 22 is the same as the height of recess 22 so that lower edges of thin spring walls 22 are substantially coplanar with the lower surface of insole 10, as shown best in FIG. 5. In the embodiment of FIGS. 1–7, thin spring walls 22 and recess 24 each have a height of approximately 1 mm and a thickness or width of approximately 1.5 mm, while the height of lower gel layer 18 in surrounding relation to recess 24 has a height of approximately 2 mm and top cover has a height of approximately 1 mm.

In the embodiment of FIGS. 1–7, thin, spaced apart spring walls 22 are formed as parallel, spaced apart, sinusoidal shaped wave patterns, although the present invention is not so limited, as will be understood from the other embodiments discussed hereinafter. Although fifteen transverse rows of thin spring walls 22 are shown with a spacing of approximately 4 mm between adjacent rows, the present invention is not so limited, and this number may vary by changing the amplitude of the sinusoidal wave patterns and/or spacing between the sinusoidal wave patterns. In addition, the pitch of the sinusoidal wave patterns in the transverse direction may also be varied.

In like manner, thin elastic and resilient spring walls 36 are formed in a repeating order within a recess 38 formed in heel portion 14. Recess 38 occupies a substantial central area of heel portion 14, with thin spring walls 36 extending substantially transversely from one side to the other side of recess 38 and integrally formed as a unitary, one-piece structure with the peripheral side wall 42 and top wall 48 of recess 38. The height of spring walls 36 is the same as the height of recess 38 so that lower edges of thin spring walls 36 are substantially coplanar with the lower surface of insole 10, as shown best in FIG. 6. In the embodiment of FIGS. 1–7, thin spring walls 36 and recess 38 each have a height of approximately 3 mm and a thickness or width of approximately 1.5 mm, while the height of lower gel layer 18 in surrounding relation to recess 38 has a height of approximately 9 mm and top cover has a height of approximately 1 mm.

In the embodiment of FIGS. 1–7, thin, spaced apart spring walls 36 are formed as parallel, spaced apart, sinusoidal shaped wave patterns, although the present invention is not so limited, as will be understood from the other embodiments discussed hereinafter. Although eleven transverse rows of thin spring walls 36 are shown with a spacing of approximately 4 mm between adjacent rows, the present invention is not so limited, and this number may vary by changing the amplitude of the sinusoidal wave patterns and/or spacing between the sinusoidal wave patterns. In addition, the pitch of the sinusoidal wave patterns in the transverse direction may also be varied.

The reason for providing thin, spaced apart spring walls in recesses 24 and 38 of toe portion 12 and heel portion 14, respectively, is that these are the areas where the major forces are exerted on insole 10 during heel impact and during push off. With this arrangement, the gel material of lower gel layer 12 is more viscous than elastic, which provides a high energy absorption by the gel. On the other hand, thin flexible and resilient spring walls 22 and 36 are more elastic than viscous, which provides a quicker acting spring than the gel of the remainder of lower gel layer 12, but with less dampening energy absorption. Thus, when a force is applied to thin spring walls 22 and 36, the response is more like a spring than as a damper, while the base gel of the remainder of lower gel layer 12 has an opposite response, that is, acting more like a damper than a spring. This combination of the more viscous base gel and the more elastic thin spring walls gives insole 10 a unique feature of a fast reaction on first heel impact and a slower higher damped energy absorption as the heel recedes into the viscous base of insole 10. When the heel recedes from insole 10, the reverse action occurs, that is, thin spring walls 36 return some of the spring action to the heel. When the foot moves to push off, the action of insole 10 is the same. In other words, this combination of the more viscous base gel and the more elastic thin spring walls 22 gives insole 10 a unique feature of a fast reaction on first forefoot impact and a slower higher damped energy absorption as the forefoot recedes into the viscous base of insole 10. When the forefoot recedes from insole 10, the reverse action occurs, that is, the thin spring walls 22 return some of the spring action to the forefoot, giving the foot a softer impact and a springy push off.

Measurements of the shock-absorbing or cushioning properties of insole 10 can be made using any suitable method, such as by using an impact tester and/or a ball rebound tester. An example of a suitable method is disclosed in "Physical Test Method PM159—Cushioning Properties," SATRA, June, 1992, pages 1–7.

The latter test is used to determine cushion energy (CE), cushion factor (CF) and resistance to dynamic compression. Cushion energy is the energy required to gradually compress a specimen of the material up to a standard pressure with a tensile testing machine. Cushion factor is a bulk material property and is assessed using a test specimen greater than sixteen millimeters thick. The pressure on the surface of the test specimen at a predefined loading is multiplied by the volume of the test specimen under no load. This pressure is then divided by the cushion energy of the specimen at the predefined load. Lastly, the resistance to dynamic compression measures changes in dimensions and in cushion energy after a prolonged period of dynamic compression.

Tests were performed to measure cushioning energy during walking and running in the heel and toe regions of solid gel insoles without thin spring walls according to the prior art and solid gel insoles 10 according to the present invention with thin spring walls 22 and 36, and the results are shown in the following Tables I–IV, were CE is the cushioning energy, that is, a measure of shock absorption and energy return, and σ is the standard deviation.

TABLE I

Cushioning Energy: Heel Region
Men's Gel Insoles

|  | CE (walking) | σ | CE (running) | σ |
|---|---|---|---|---|
| prior art | 13.1 | 0.3 | 42.1 | 1.2 |
| present invention (with spring walls) | 99.6 | 1.3 | 194.6 | 7.8 |

TABLE II

Cushioning Energy: Toe Region
Men's Gel Insoles

|  | CE (walking) | σ | CE (running) | σ |
|---|---|---|---|---|
| prior art | 13.5 | 0.1 | 43.0 | 1.4 |
| present invention (with spring walls) | 30.5 | 1.2 | 45.8 | 2.1 |

TABLE III

Cushioning Energy: Heel Region
Women's Gel Insoles

|  | CE (walking) | σ | CE (running) | σ |
|---|---|---|---|---|
| prior art | 14.8 | 0.7 | 46.9 | 1.9 |
| present invention (with spring walls) | 58.0 | 5.0 | 101.0 | 8.2 |

TABLE IV

Cushioning Energy: Toe Region
Women's Gel Insoles

|  | CE (walking) | σ | CE (running) | σ |
|---|---|---|---|---|
| prior art | 11.1 | 0.1 | 35.2 | 4.8 |
| present invention (with spring walls) | 37.1 | 0.9 | 60.9 | 1.6 |

It will be appreciated from the above that there is a substantial increase in the cushioning energy of insoles 10 with thin spring walls 22 and 36 according to the present invention in comparison with conventional gel insoles that do not include the thin spring walls.

Figure 8:
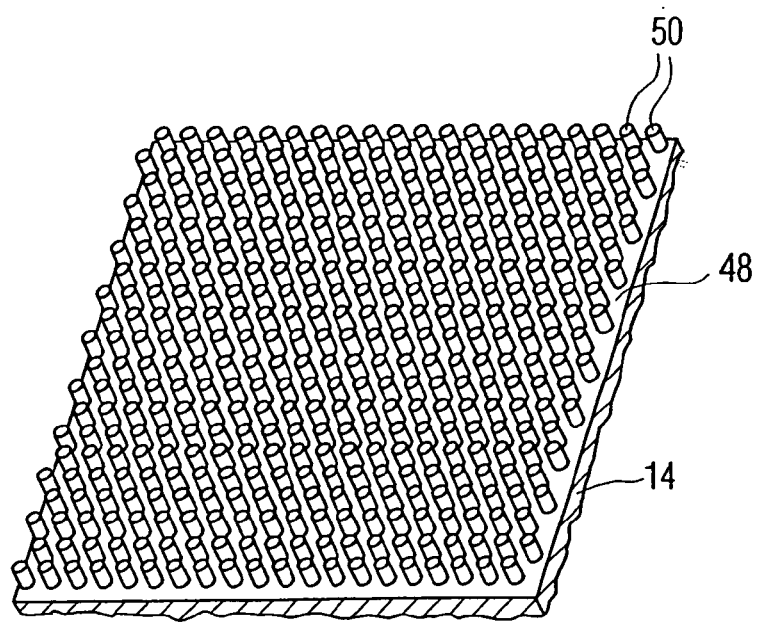
FIG. 8 is an enlarged perspective view of a cut-away portion of thin spring walls at the bottom of the heel of another embodiment of the present invention, and having a cylindrical column pattern.
Figure 9:
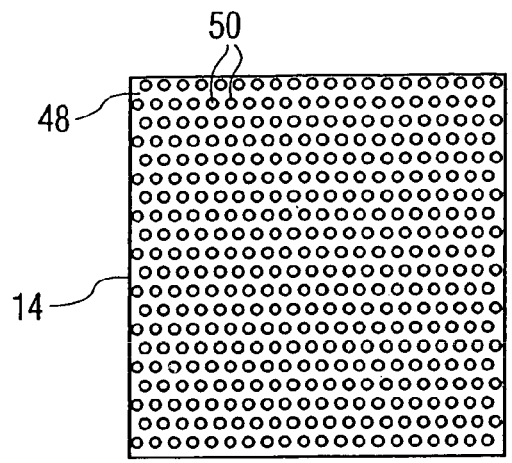
FIG. 9 is a bottom plan view of the cut-away portion of the thin spring walls of FIG. 8.

Although thin, spaced apart spring walls 22 and 36 have been shown in a sinusoidal wave pattern, such thin spring walls can take other shapes, such as the columnar shape of FIGS. 8 and 9, that is, formed as a plurality of parallel, spaced apart, discrete cylindrical columns 50 in each recess 24 and 38, with lower edges thereof being substantially coplanar with the lower surface of insole 10 in surrounding relation to the recess, in the same manner as spring walls 22 and 36. In such case, the diameter of each column 50 is preferably much less than the height of each column, for example, in the ratio of approximately 1:2 to 1:4.

Figure 10:
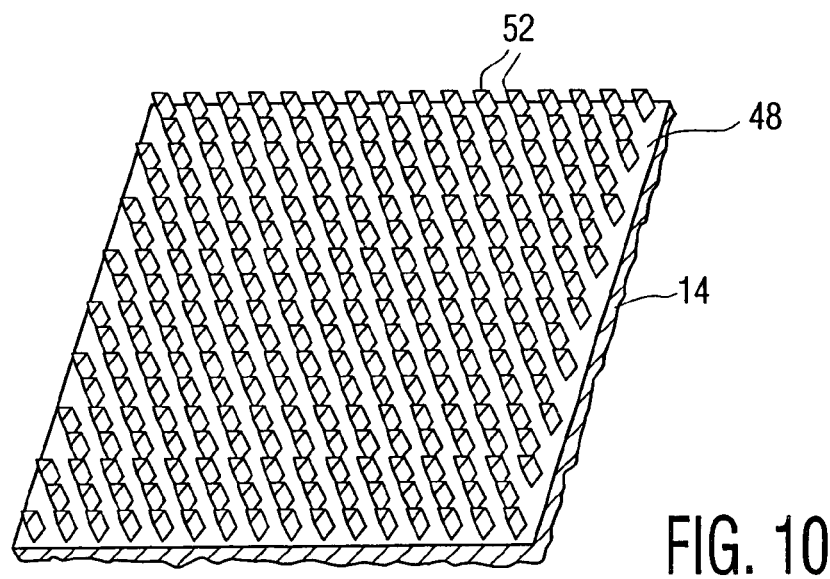
FIG. 10 is an enlarged perspective view of a cut-away portion of thin spring walls at the bottom of the heel of still another embodiment of the present invention, and having a triangular column pattern.
Figure 11:
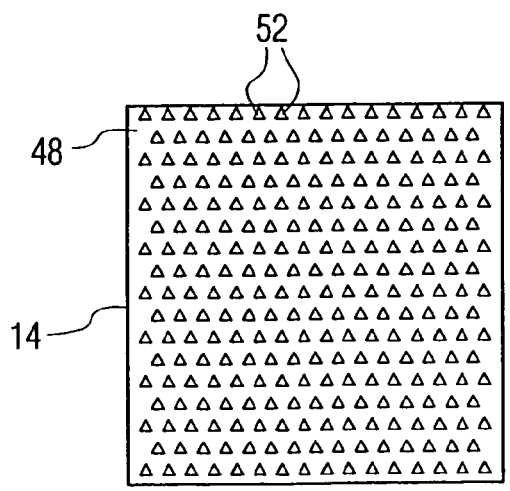
FIG. 11 is a bottom plan view of the cut-away portion of the thin spring walls of FIG. 10.

As another alternative embodiment, the thin spring walls can have the columnar shape of FIGS. 10 and 11, that is, formed as a plurality of parallel, spaced apart, discrete columns 52 but with triangular sectional configurations, in each recess 24 and 38, with lower edges thereof being substantially coplanar with the lower surface of insole 10 in surrounding relation to the recess, in the same manner as spring walls 22 and 36. In such case, the length of any triangular side of each column 52 is preferably much less than the height of each column, for example, in the ratio of approximately 1:2 to 1:4.

Figure 12:
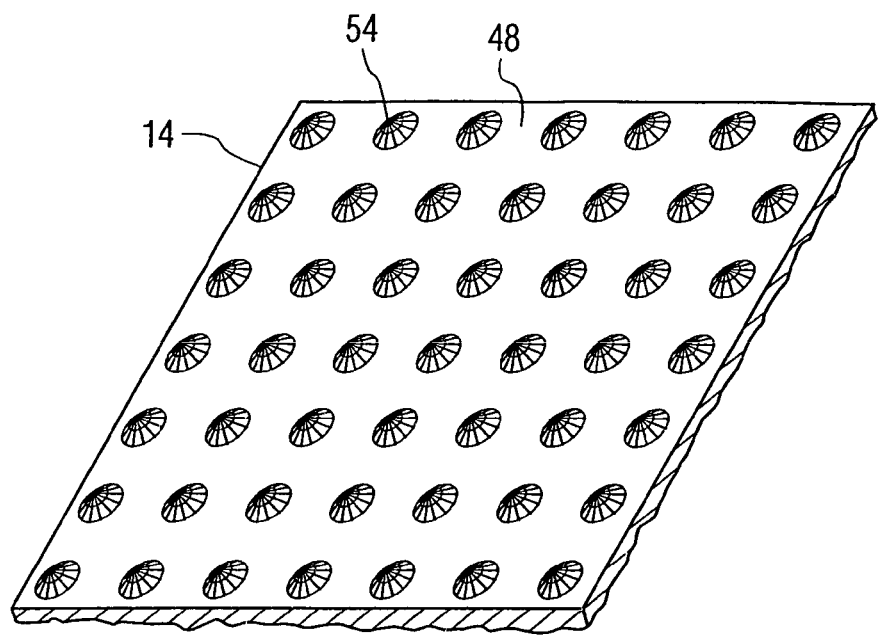
FIG. 12 is an enlarged perspective view of a cut-away portion of spring walls at the bottom of the heel of yet another embodiment of the present invention, and having a hemispherical shape.
Figure 13:
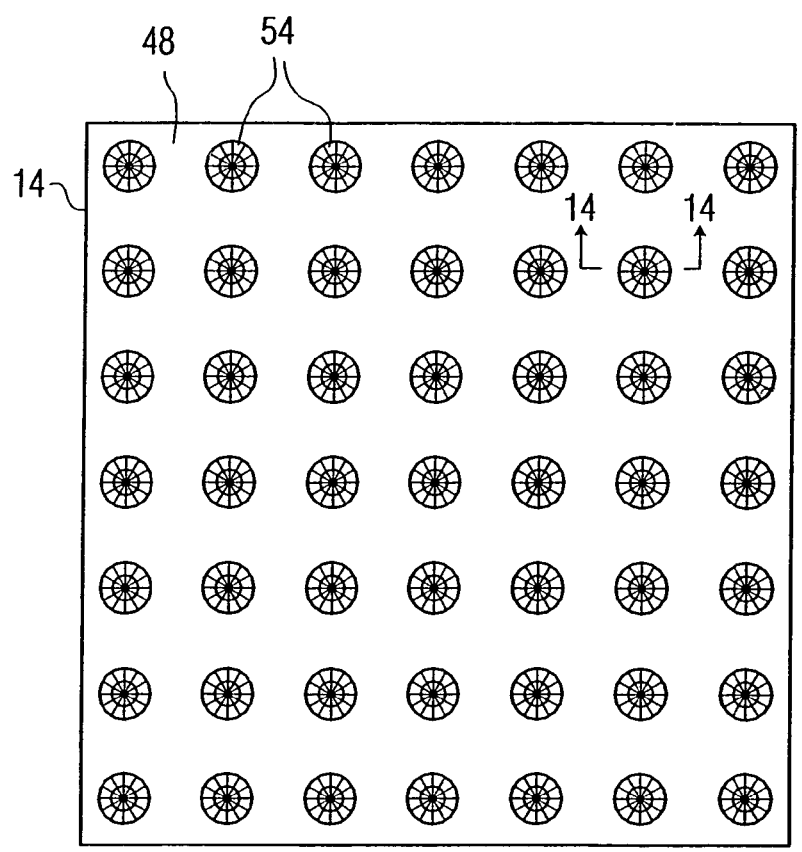
FIG. 13 is a bottom plan view of the cut-away portion of spring walls of FIG. 12.
Figure 14:
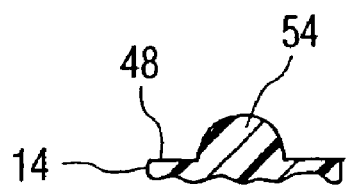
FIG. 14 is a cross-sectional view of the cut-away portion of FIG. 13, taken along line 14—14 thereof.
Figure 15:
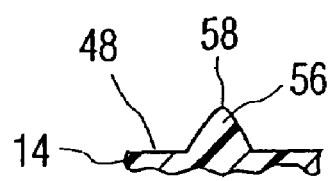
FIG. 15 is a cross-sectional view similar to FIG. 14, but showing a modification of the spring walls thereof.

As another alternative embodiment, the thin spring walls can have the hemispherical shape of FIGS. 12–14, that is, formed as a plurality of spaced apart hemispheric shaped walls 54 in each recess 24 and 38, with lower edges thereof being substantially coplanar with the lower surface of insole 10 in surrounding relation to the recess, in the same manner as spring walls 22 and 36. Alternatively, in place of hemispherical shaped walls 54, the shape can be varied slightly to present substantially conical shaped walls 56 with rounded free ends 58, as shown in FIG. 14.

The different geometries of the spring walls are provided for different insoles in order to vary the spring and cushioning effects.

Figure 17:
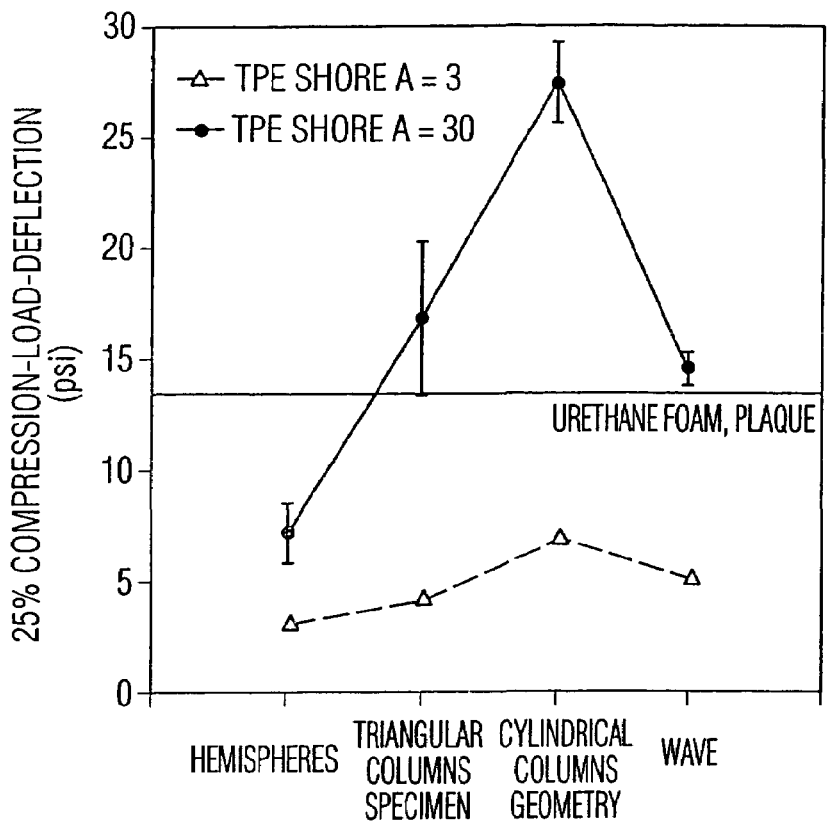
FIG. 17 is a graphical diagram of 25% compression-load-deflection versus different geometries of the spring walls.

In this regard, FIG. 17 shows a graphical diagram of 25% compression-load-deflection versus different geometries of insole 10 at the position of the spring walls. This is a static load test that shows the static support that insole 10 provides for the different geometries of hemispheric shaped walls 54, triangular column walls 52, cylindrical column walls 50 and sinusoidal wave walls 22, 36. This test measures the force or load necessary to deflect insole 10 at the plantar surface of the foot, and thereby measures the amount of static support that insole 10 provides.

The solid line, inverted check mark plot was performed with a gel having a TPE Shore A hardness of 30. As clearly seen, the best static support occurs with cylindrical columns 50. The dashed line plot was performed with a gel having a TPE Shore A hardness of 3. The best static support again occurs with cylindrical columns 50, and the worst static support occurs with hemispheric shaped walls 54. The horizontal line at approximately 14 psi is a comparison line obtained with a plaque or section of constant urethane foam according to the prior art.

Figure 18:
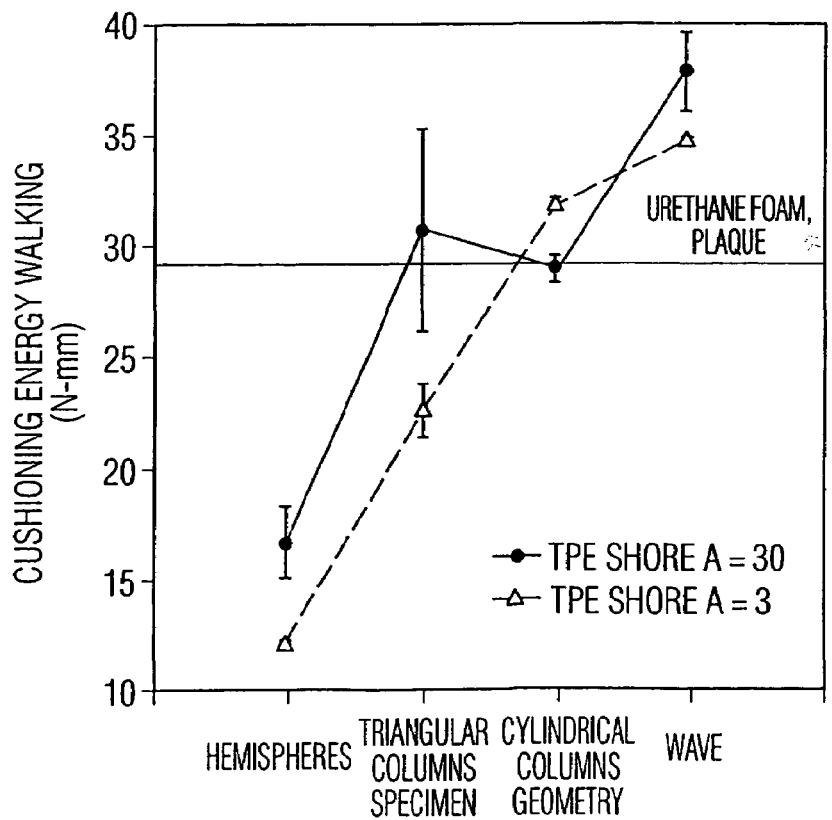
FIG. 18 is a graphical diagram of cushioning energy walking versus different geometries of the spring walls.

FIG. 18 shows a graphical diagram of cushioning energy walking versus different geometries of the thin spring walls. This is a test of the shock absorption and energy return of insole 10 at the spring walls for the different geometries of hemispheric shaped walls 54, triangular column walls 52, cylindrical column walls 50 and sinusoidal wave walls 22, 36 at the plantar surface of the foot.

The solid line plot was performed with a gel having a TPE Shore A hardness of 30. As clearly seen, the best spring action occurs with the sinusoidal wave spring walls 22, 36, while the worst spring action again occurs with hemispheric shaped walls 54. The dashed line plot was performed with a gel having a TPE Shore A hardness of 3. The best spring action again occurs with spring walls 22, 36. The horizontal line at approximately 29 N-mm is a comparison line obtained with a plaque or section of constant urethane foam according to the prior art.

Figure 19:
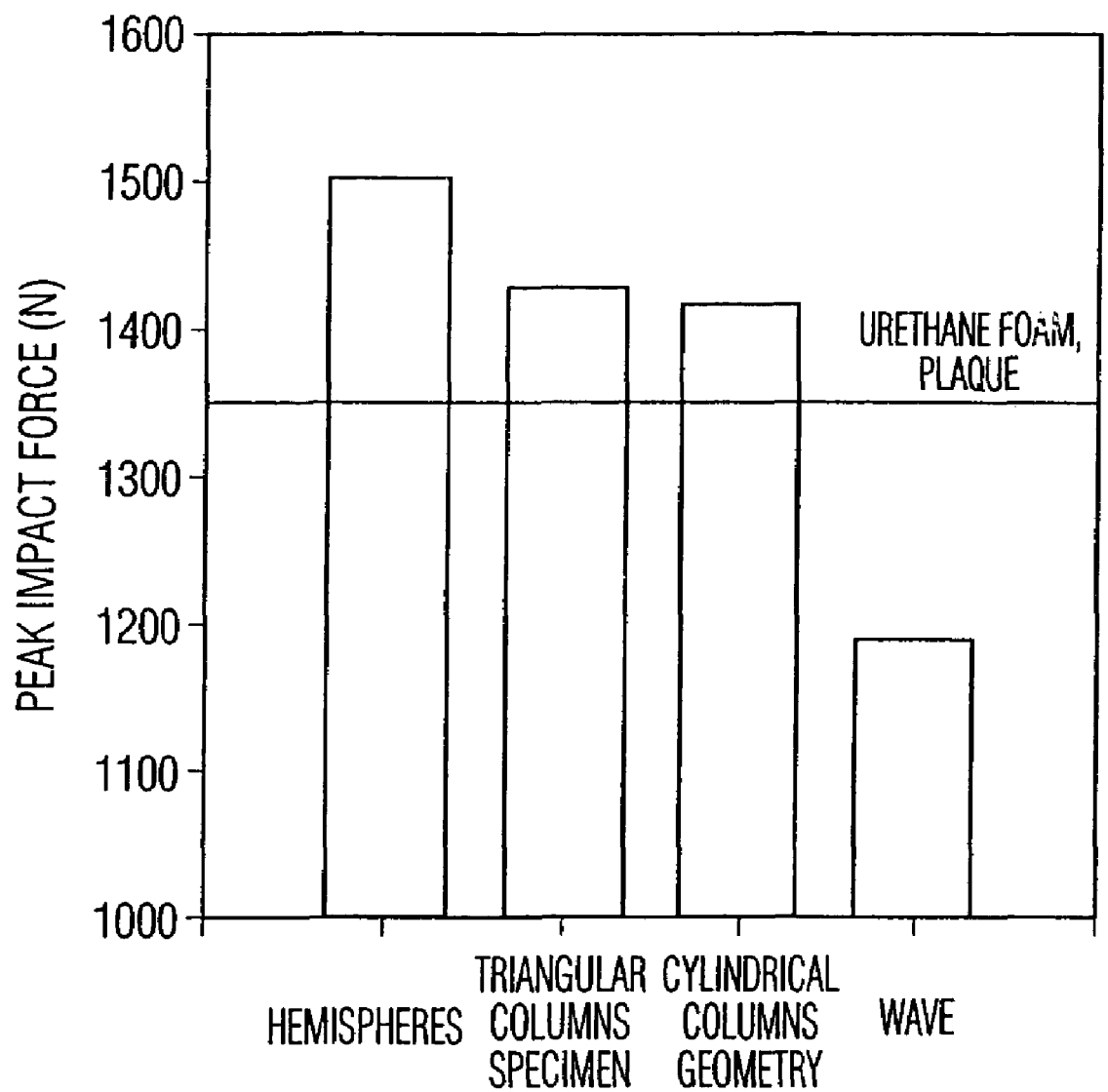
FIG. 19 is a graphical diagram of peak impact force versus different geometries of the spring walls.

FIG. 19 shows a graphical diagram of peak impact force versus different geometries of insole 10 at the position of the spring walls. This is a dynamic load test that shows the dynamic support that insole 10 provides for the different geometries of hemispheric shaped walls 54, triangular column walls 52, cylindrical column walls 50 and sinusoidal wave walls 22, 36. This test measures the ability to absorb shock during walking or running at the plantar surface of the foot.

As clearly seen, the different geometries of the spring walls can spread the impact forces over a large surface area, thereby decreasing the peak impact load.

From the above, it is clearly seen that different geometries can be selected for different purposes, that is, to varying the static cushioning, dynamic cushioning and spring effect.

Top layer 20 can be made from any suitable material such as fabric, leather, leatherboard, expanded vinyl foam, flocked vinyl film, coagulated polyurethane, latex foam on scrim, supported polyurethane foam, laminated polyurethane film or in-mold coatings such as polyurethane, styrene-butadiene-rubber, acrylonitrile-butadiene, acrylonitrile terpolymers and copolymers, vinyls, or other acrylics, as integral top covers. Desirable characteristics of top cover 20 include good durability, stability and visual appearance. Also desired is that the material of top cover 20 have good flexibility, as indicated by a low modulus, in order to be easily moldable. The bonding surface of top cover 20 should provide an appropriate texture in order to achieve a suitable mechanical bond to lower gel layer 12. Preferably, top cover 20 is a fabric, such as a brushed knit laminate top cloth (brushed knit fabric/urethane film/non-woven scrim cloth laminate) or a urethane knit laminate top cloth.

Figure 2:
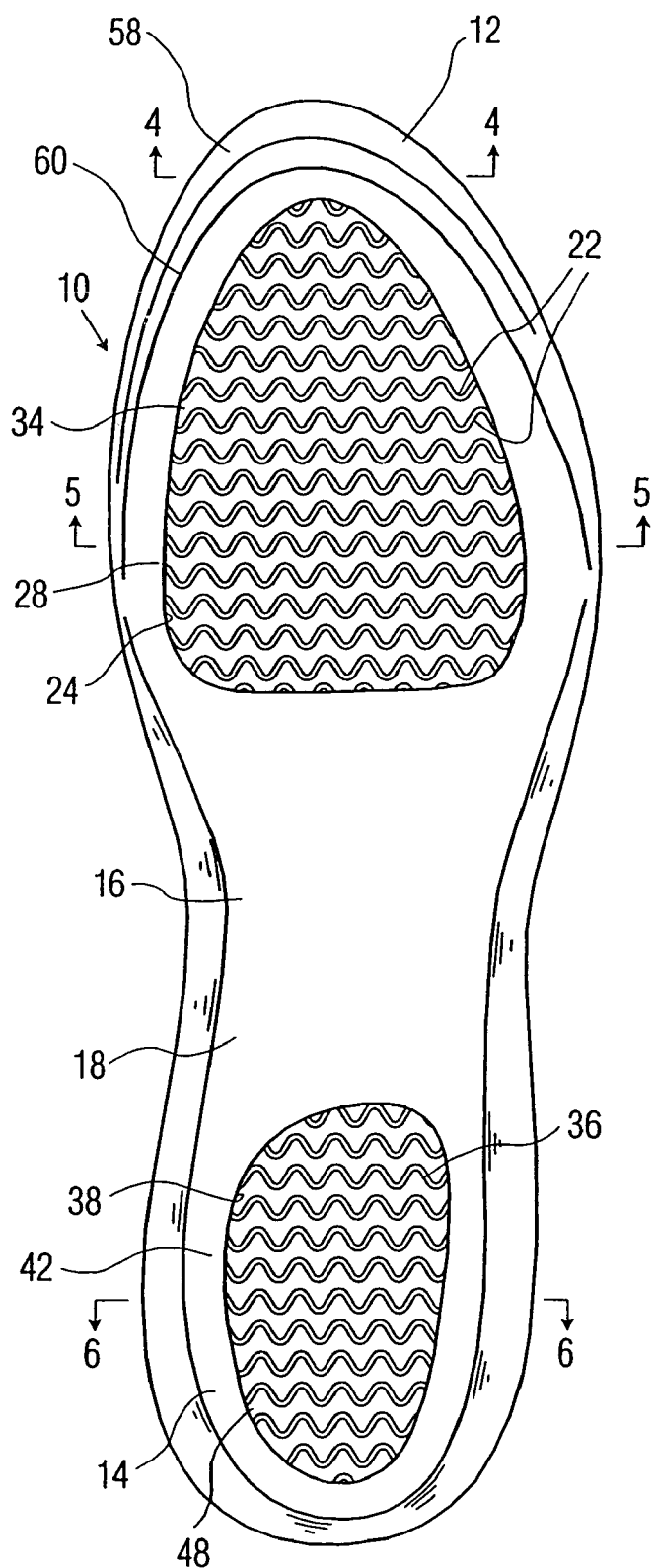
FIG. 2 is a bottom plan view of the gel insole.
Figure 3:
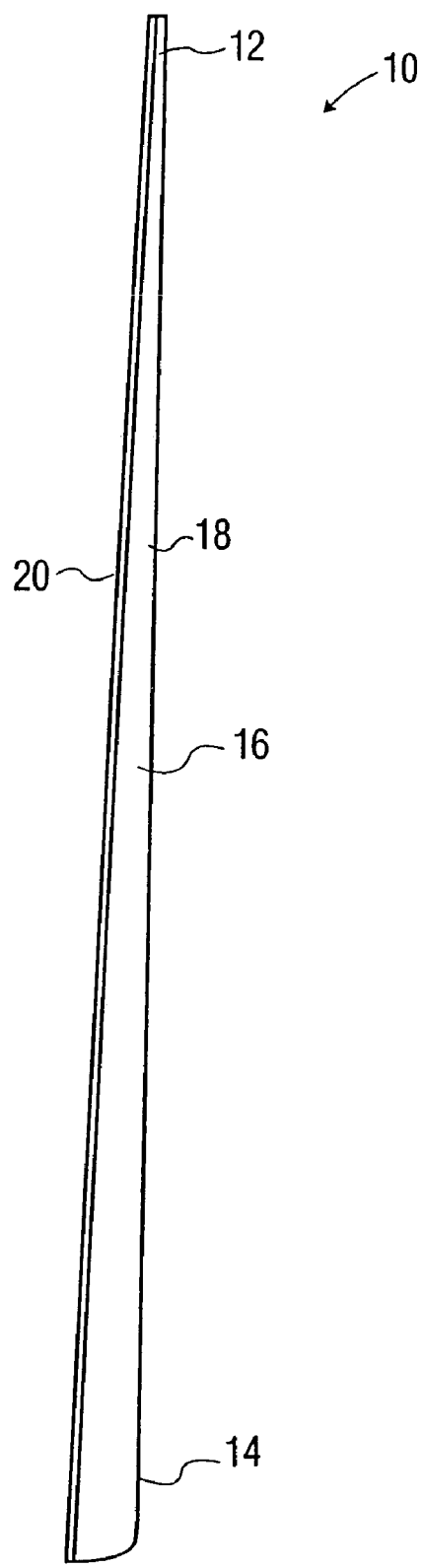
FIG. 3 is a side elevational view of the gel insole.
Figure 4:
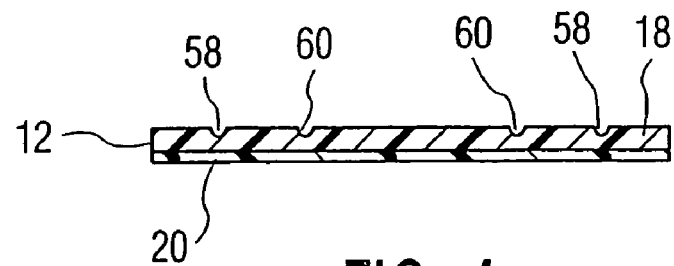
FIG. 4 is a cross-sectional view of the gel insole, taken along line 4—4 of FIG. 2.
Figure 5:
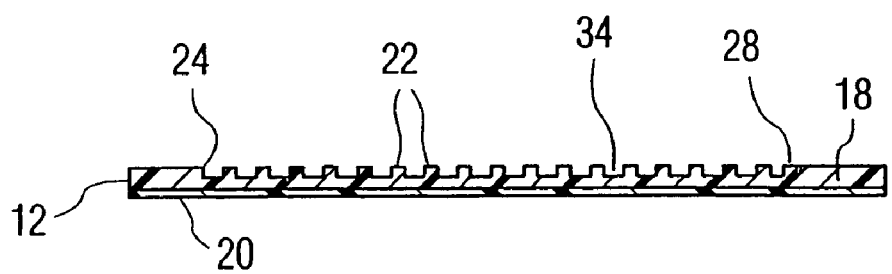
FIG. 5 is a cross-sectional view of the gel insole, taken along line 5—5 of FIG. 2.
Figure 6:
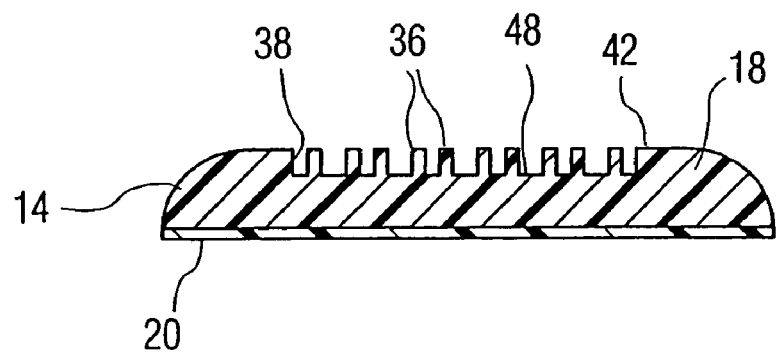
FIG. 6 is a cross-sectional view of the gel insole, taken along line 6—6 of FIG. 2.
Figure 7:
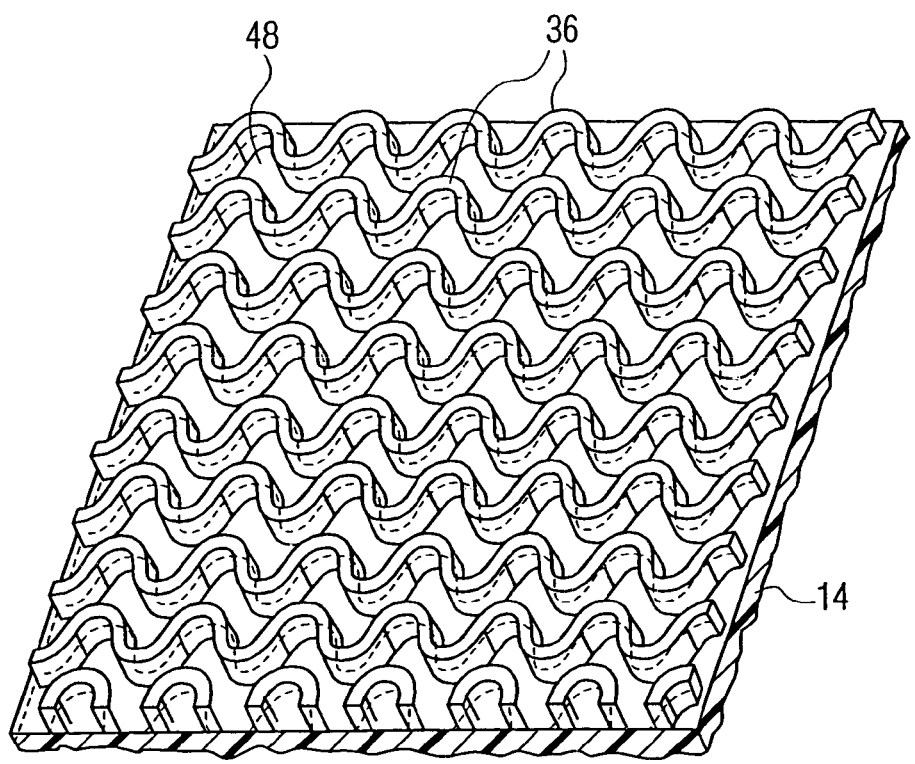
FIG. 7 is an enlarged perspective view of a cut-away portion of the thin spring walls at the bottom of the heel, having a sinusoidal wave pattern.

Typically, insole 10 would be sized corresponding to shoe sizes and would be provided in sized pairs. Alternatively, insole 10 may be trimmed to the requirements of the user. In this regard, arcuate pattern trim lines 58 and 60 may be formed on the lower surface of toe portion 12 of insole 10, and which are representative of various sizes of the human foot. For example, insole 10 may be provided for a men's shoe size of 11–12, with first continuous pattern trim line 58 being representative of a smaller size insole for a men's shoe size 9–10, and second continuous pattern trim line 60 extending around the periphery of toe portion 12 indicative of another size of insole for a men's shoe size 7–9. If the user requires a size other than the original large size, the wearer merely trims the insole with a scissors or cutting instrument, using pattern trim line 58 or 60, to achieve the proper size. The pattern trim lines may be imprinted by conventional printing techniques, silkscreening and the like. As an alternative, pattern trim lines 58 and 60 may be formed as shallow grooves, as shown in FIGS. 2 and 4, or be perforated, so that a smaller size insole may be separated by tearing along the appropriate trim lines, which tearing operation is facilitated by the inclusion of perforations.

Although the present invention has been disclosed relative to a full length insole, it will be appreciated that an insole according to the present invention can be made other than a full length insole, such as a three quarter length insole, that is, where the length extends from the heel to the first metatarsals of the foot, or any other suitable arrangement.

Figure 16:
FIG. 16 is a cross-sectional view of a heel portion of a gel insole according to another embodiment of the present invention.

Further, although heel portion 14 has been shown to have a uniform height along the entire width thereof, other variations may be provided, as shown in FIG. 16, in which heel portion 14 has sloping side edges and in which the width decreases toward the middle thereof.

Although the present invention uses the term insole, it will be appreciated that the use of other equivalent or similar terms such as innersole or insert are considered to be synonymous and interchangeable, and thereby covered by the present claimed invention.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. A removable insole for insertion into footwear, comprising a lower layer made of a viscoelastic gel and including:
   a lower surface;
   an upper surface;
   at least one of a toe portion and a heel portion formed from said viscoelastic gel,
   at least one recess in the lower surface of said at least one of a toe portion and a heel portion, each said recess having a peripheral side wall and a top wall, and
   a plurality of spaced apart spring walls formed from said viscoelastic gel in each said recess, said spring walls being connected with said top wall of a respective said recess, said spring walls having lower edges generally coplanar with a lower surface of said at least one of a toe portion and a heel portion which is in surrounding relation to the respective said recess, wherein each said spring walls consists of a generally sinusoidal wave shape.

2. A removable insole according to claim 1, wherein, when said at least one recess is formed in the heel portion, each of said spring walls has a height in a first direction which is greater than a width thereof in a direction transverse to said first direction.

3. A removable insole according to claim 2, wherein said spring walls are connected with said peripheral side wall and said top wall of the respective said recess.

4. A removable insole according to claim 1, wherein said plurality of spring walls are formed in substantially parallel, spaced apart relation.

5. A removable insole according to claim 1, wherein, when said at least one recess is formed in the heel portion, each of said spring walls has a height in a first direction which is greater than a width thereof in a direction transverse to said first direction.

6. A removable insole according to claim 5, wherein a spacing between adjacent ones of said spring walls is greater than the width of said spring walls.

7. A removable insole according to claim 6, wherein said column members are in parallel, spaced apart relation.

8. A removable insole according to claim 1, wherein said spring walls are formed as column members.

9. A removable insole according to claim 8, wherein, when said at least one recess is formed in the heel portion, each of said spring walls has a height in a first direction which is greater than a width thereof in a direction transverse to said first direction.

10. A removable insole according to claim 8, wherein a spacing between adjacent ones of said spring walls is greater than the width of said spring walls.

11. A removable insole according to claim 8, wherein said spring walls are connected with said top wall of the respective said recess.

12. A removable insole according to claim 1, further comprising at least one pattern trim line at the toe portion for trimming the insole to fit into smaller size footwear.

13. A removable insole according to claim 1, wherein said lower layer includes said toe portion, said heel portion and a medial arch portion interconnecting said toe portion and said heel portion, with a first said recess with said spring walls in said toe portion and a second said recess with said spring walls in said heel portion.

14. A removable insole according to claim 13, wherein said heel portion has a greater thickness than said toe portion, and said spring walls in said second recess having a greater height than said spring walls in said first recess.

15. A removable insole according to claim 12, wherein opposite sides of said medial arch portion and opposite sides and a rear end of said heel portion gently slope downwardly and inwardly toward the lower surface of said lower layer.

16. A removable insole according to claim 1, further comprising a top cover secured to the upper surface of said lower layer.

* * * * *